United States Patent [19]
Roggenstein et al.

[11] 3,942,369
[45] Mar. 9, 1976

[54] METHOD OF AND APPARATUS FOR MEASURING AND SETTING THE TENSION OF STRESSED MEMBERS

[75] Inventors: Edwin O. Roggenstein, Birmingham; Donald Allen Andrews, Brighton; Chockalingam Manthiram, Plymouth, all of Mich.

[73] Assignee: Burroughs Corporation, Detroit, Mich.

[22] Filed: Aug. 26, 1971

[21] Appl. No.: 175,060

[52] U.S. Cl. .................................. 73/143; 73/67.2
[51] Int. Cl.² ........................................ G01N 29/00
[58] Field of Search ................ 73/DIG. 1, 67.2, 143

[56] References Cited
UNITED STATES PATENTS

| | | | |
|---|---|---|---|
| 1,869,884 | 8/1932 | Curtis .............................. | 73/67.2 X |
| 1,908,258 | 5/1933 | Klopsteg ........................ | 73/67.2 X |
| 2,278,510 | 4/1942 | Condon .......................... | 73/67.2 |
| 2,618,970 | 11/1952 | Hitchcock et al. .............. | 73/67.2 X |

Primary Examiner—Jerry W. Myracle
Attorney, Agent, or Firm—Ralzemond B. Parker; Edwin W. Uren; Paul W. Fish

[57] ABSTRACT

Resonant vibration is employed for imparting oscillations to a stressed wire, cable or metallic strip for the purpose of measuring its tension or for setting the vibrated member at a desired tension. A U-shaped magnetic resonator has an air gap to receive a stressed wire or cable and to impart vibrations thereto, the air gap being of such a width as to permit the received element to vibrate freely at its resonant frequency. The tension of the stressed element can be measured by varying the frequency of the resonator and noting when the condition of resonance exists or the tension of the element may be set by varying its tension while subjected to a steady predetermined pulsating magnetic flux field until the condition of resonance is noted. Either operation is performed in the absence of current flow through the stressed element.

10 Claims, 6 Drawing Figures

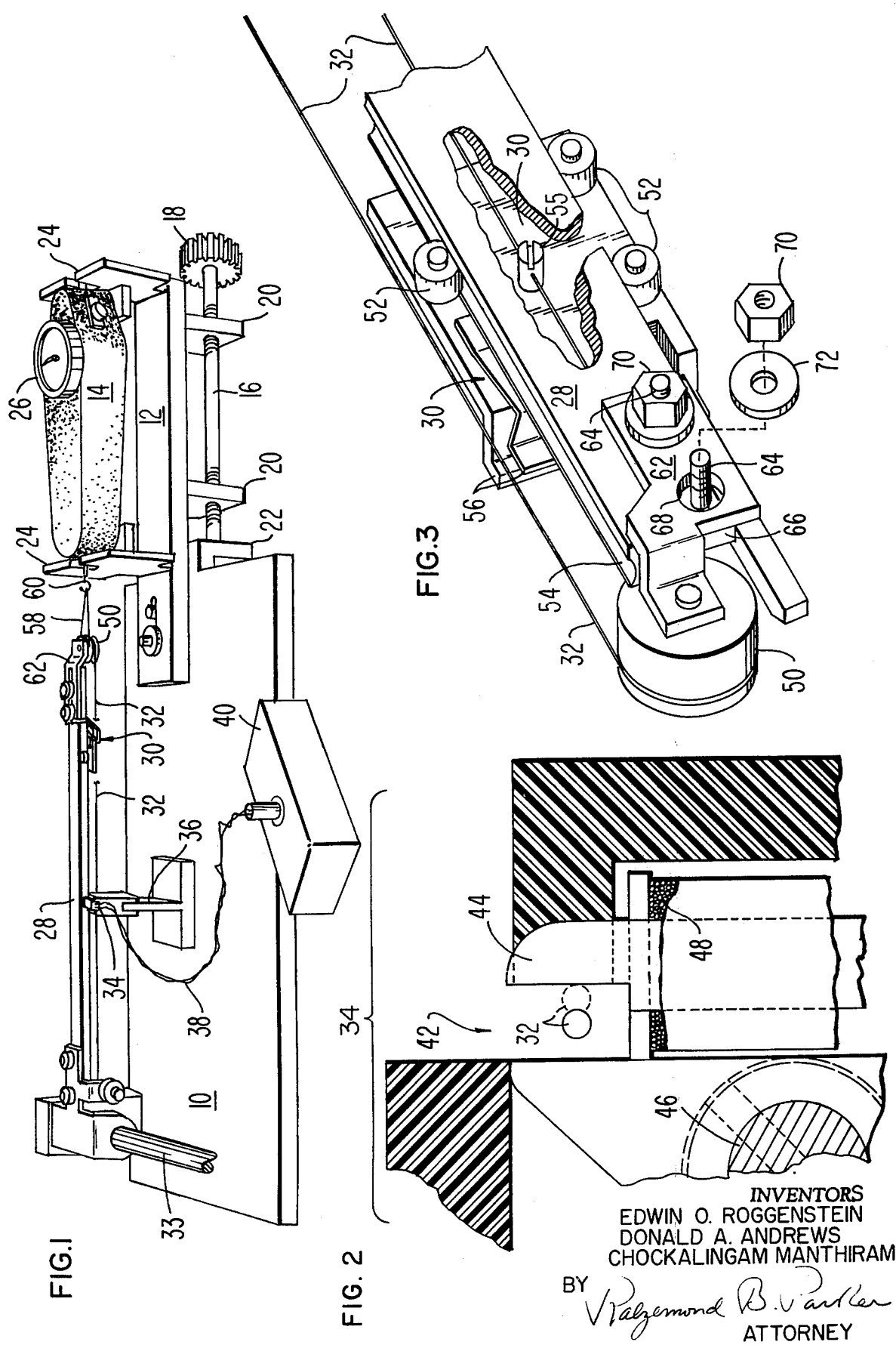

METHOD OF AND APPARATUS FOR MEASURING AND SETTING THE TENSION OF STRESSED MEMBERS

BACKGROUND OF THE INVENTION

This invention is directed to that field of art pertaining to the measurement and setting of the tension of a stressed member such as a wire or cable.

SUMMARY OF THE INVENTION

An important object of the invention is to provide an improved method of and apparatus for measuring and setting the tension of a stressed member, such as a wire or cable.

Another important object is to provide an improved method of and apparatus for producing accurately tensioned wire or cable members enabling the use of a simple and economical procedure and equipment for this purpose.

In carrying out these objects, the present invention contemplates the utilization of a magnetic transducer shaped to partially surround a stressed member, such as a cable or wire element, and by pulsing the magnetic flux field thereof to either measure or set the tension of the member at the time its condition of resonance is exhibited.

More particularly, the invention contemplates a resonator having an air gap of such size to receive a tensioned member and to permit it to oscillate at its natural frequency therewithin, the resonator being driven by an oscillator that produces pulsations in the magnetic field of the resonator for attracting the stressed member at the driving frequency of the oscillator. Provision is made for either varying or adjusting the tension of the stressed member until a condition of resonance is exhibited by the large vibrating displacement of the stressed member and for varying the frequency of the oscillator until the resonant frequency of the stressed member is reached at which time its tension will be noted. The invention finds particular usage in the setting of stressed wires or cables employed for controlling the movements and positioning of bodies along predefined paths where precise movements are necessary and especially where several similarly tensioned members are employed in either the same or like equipment.

Apparatus designed for the above objects can be fabricated from comparatively simple components and can be operated by relatively semi-skilled operators, yet having the important advantage of precisely determining the tension of a stressed member or of accurately setting it in a desired tensioned condition simply by visual observation.

The above listed objects and advantages, and other objects, advantages and aspects of the invention, will be more fully explained in the following detailed description. For a more complete understanding of the invention, reference may be had to the following detailed description in conjuction with the drawings.

BRIEF DESCRIPTION OF THE DRAWINGS

FIG. 1 is a perspective view of a fixture designed for measuring the tension of a stressed member in accordance with this invention, and particularly illustrating the utilization of the equipment for measuring the tension of a tensioned cable for moving an object along a track or bar;

FIG. 2 is an enlarged fragmentary cross-sectional view of the air-gap area of a magnetic frequency transducer, the air-gap serving to receive the stressed member;

FIG. 3 is a perspective view of a carriage movable along a track or a bar controlled by a tensioned cable and for which the invention is applicable;

DESCRIPTION OF A PREFERRED EMBODIMENT OF THE INVENTION

Figure 5:
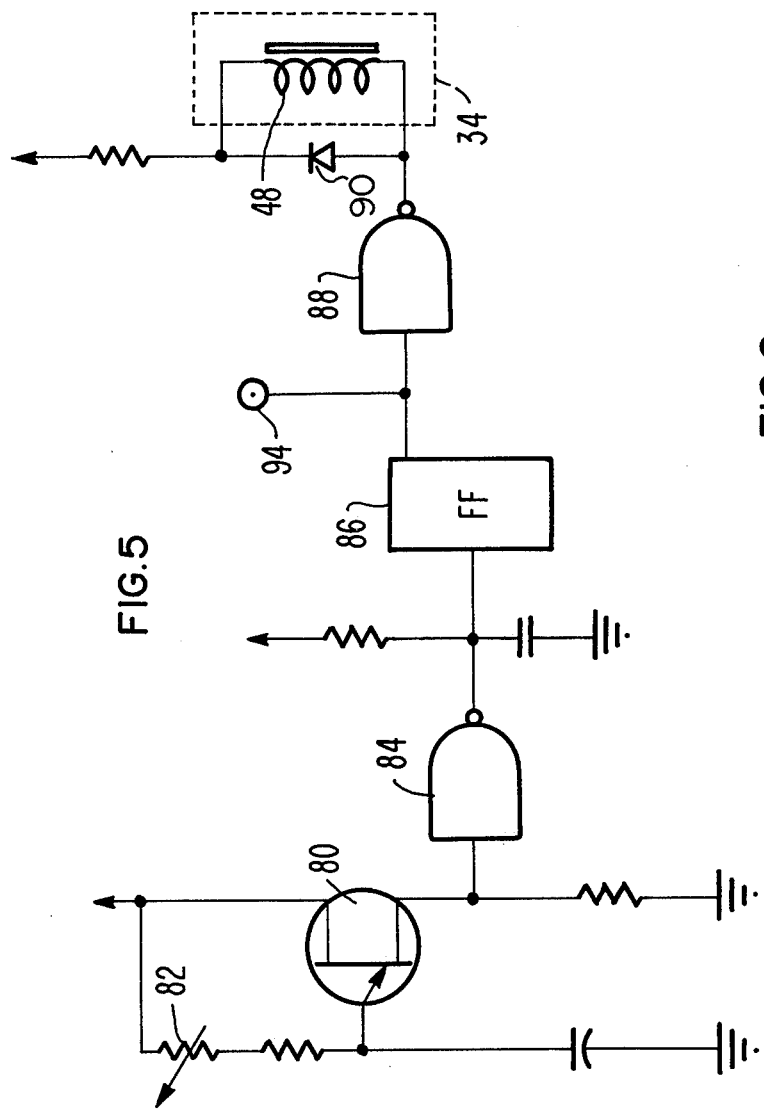
FIG. 5 illustrates a preferred oscillator circuit for operating the frequency transducer.

The invention is particularly useful in setting the tension of a cable, wire or tape, which may be of cylindrical or flat metallic stock, and which is designed to control the motion of a part of an apparatus where precise movement and subsequent stationary positioning of the part is extremely important. One such example is a carriage employed in the ledger transport system of data processing apparatus for advancing and retracting a document gripping device, as disclosed in the co-pending application for patent filed in the names of Harold M. Frederick and Edward A. Nicol, Ser. No. 52,612, filed July 6, 1970, now U.S. Pat. No. 3,663,010, and of common ownership herewith. The invention is also usable in setting the tensions of flexible elements such as the metallic retaining tapes used for controlling the angular motions of ball-type printing heads employed in typewriters and similar equipment for the printing of characters.

With reference to FIG. 1, there is illustrated a suitable fixture for both measuring and setting the tensions of such motion controlling cables and tapes. The fixture includes a supporting base plate 10 to one side of which is secured an extension 12 cradling a force gage 14 of conventional construction. The extension 12 is adjustably movable relative to the base plate and in a straight line parallel to the plate thereof. For this purpose, a screw member 16 having fine threads on its shank and a knurled head 18 may be provided. The screw 16 is threaded into one or more flanges 20—20 of the extension and its inner end is in abutting engagement with a depending flange of the base plate such as exhibited at 22. Two upright members 24—24 on the extension provide the cradle for mounting the force gage 14, the latter having dial 26 from which readings in pounds may be made for indicating the varying tensions being applied to the cable or tape being subjected to test or setting.

The fixture of FIG. 1 illustrates equipment which may be used for both testing and setting of a cable utilized in the data processing equipment of the aforesaid patent for moving one of the document gripping devices disclosed therein. More specifically, the subject matter of the mechanism to be tested and adjusted comprises an elongated rod or bar 28 of rectangular cross-section forming a track along which a carriage 30 is movable from one end to the other end thereof. A looped metallic cable 32 extends the length of the track member 28 and has its opposie end portions reversely wound around individual winding drums, one of which is represented at 76 in FIG. 4, secured to a driving shaft 33. Rotation of the shaft will cause the drums to pay out one cable section while the other cable section is pulled in. A midportion of the cable is fixed to the carriage 30 with the result that rotation of the shaft in one or the other direction will cause the carriage to move back and forth on the track member 28.

Figure 4:
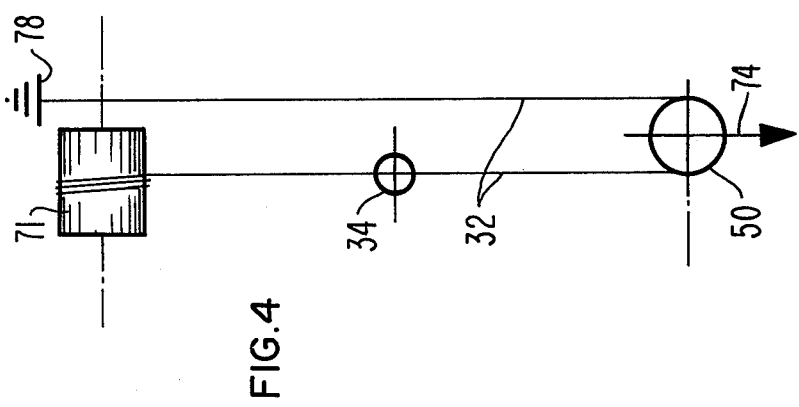
FIG. 4 is a schematic view of a cable system for moving the object along the bar of FIG. 1 and showing the location of the magnetic frequency transducer.

Approximately midway of one section of the cable 32 is a magnetic resonator generally indicated at 34 in FIGS. 1 and 4 and shown supported from the base plate 10 by a standard 36. The resonator has a portion thereof shaped to partially surround the cable 32 to apply a pulsating magnetic flux thereto. The resonator is connected by lead wires 38 to a variable frequency oscillator 40 which may be of conventional construction for establishing the frequency of the pulsating magnetic field.

FIG. 2 illustrates in enlarged scale the cable embracing portion of the resonator 34. The upper portion of the resonator is stepped and shaped with an upwardly opening air gap 42 into which the wire or cable element 32 is received as illustrated in FIG. 2. The air gap is especially shaped so as to permit the cable to freely vibrate at its resonant condition, one extreme position being illustrated in dotted outline in the gap. The vibrating resonator may be fabricated from a magnetic tape read/write head customarily used in the electronic computing field for recording upon or reading from magnetic tapes. Such a head is usually formed of a plurality of generally U-shaped, magnetically permeable laminations, one lamination of which is illustrated at 44. The laminations may be compactly held together by a screw member 46 extending through the laminations and threadedly engaged in the resonator housing. A wire coil 48 surrounds a common leg portion of the laminations in the manner shown in FIG. 2 to which the leads 38 are connected. It is apparent that the oscillator will produce a pulsating current in the coil 48 and this in turn will generate a pulsating magnetic field in the air gap in which the cable is received and produce vibrations in the cable. It is only at the natural frequency of the stressed cable that the displacement of the cable will become large and clearly visible, indicating that the frequency of the alternations in the magnetic field coincides with the natural frequency of the stressed cable.

FIG. 3 illustrates in enlarged scale the forward end of the track member 28 where the cable 32 is shown wound around a pulley 50 fixed to the extremity of the track member. Suspended under the track member is the carriage 30 which includes three wheels or rollers 52 disposed in the manner shown on opposite sides of the track member 28 and guided along the side edges thereof to provide the to and fro motion of the carriage along the track. For the desired precise movement, as well as for the purpose of suspending the carriage 30 under the track member, the side edges of the member may be concavely shaped as shown at 54 and the rollers 52 may have their peripheries complementarily rounded to ride in these concave edges. The track member 28 is broken away in FIG. 3 to show the securement of the inside section of the cable 32 to the carriage 30 in the manner as indicated by stud 55. The forward end of the carriage is provided with a pair of jaws 56 which when the carriage is at the outer end of the track will open to receive and later close to grip the leading edge of a document, such as a magnetic striped ledger, and thereafter to control the movement of the same forwardly and rearwardly along the track member 28.

When such a track member and its associated parts are mounted on the fixture illustrated in FIG. 1, the forward are mounted on the fixture illustrated in FIG. 1, the forward end of the track member bearing the pulley 50 is brought up close to the cradle and in alignment with the force gage 14. A small endless loop of wire indicated at 58 is connected at one end to the track member 28, such as by partially encircling the pulley 50 or its stub shaft and connected at its other end to a hook 60 attached to the interior mechanism of the force gage. It is to be understood that a plate 62 carries the pulley 50 and is adjustably mounted on the extremity of the track member by a pair of nut and bolt assemblies, one of which is shown in exploded relation in FIG. 3. Actually, each bolt is in the form of a threaded stud 64 having a rectangular head 66 fitting the underside channel of the track member preventing its rotation and any movement other than in the direction of the track formed by the bar 28. The studs extend upwardly through oversize holes 68 in the track member to provide the desired amount of adjustment of the plate 62 relative to the track member. A nut 70 and washer 72 complete the fastening assembly. Normally the plate 62 is rigidly secured to the track member by the pair of nut and bolt assemblies 64–72. However, for the purpose of testing the tension of the cable as well as setting it at the desired tension, the two nuts 70—70 are loosened sufficiently to release the plate 62 for movement relative to the track member 28 as the screw 16 associated with the force gage is rotated to shift the gage relative to the base support. Such movement of the gage, acting through the connection formed by the endless loop 58 and the hook 60, will be opposed by the tensioned cable 32 and therefore the plate 62 will move only very slightly in one direction or the other depending upon whether the force applied by the gage 14 is in an increasing or decreasing direction. The dial 26 of the gage will indicate the extent of force being applied.

FIG. 4 schematically illustrates a cable system similar to that employed in FIG. 1 where a force acting on the pulley 50 of plate 62 in the direction of the arrow 74 will increase the tension on the stressed cable 32, assuming the winding drum 71 is held against rotation. The force gage 14 is capable of doing this when the screw 16 is rotated in the direction to shift the gage away from the support plate 10. FIG. 4 illustrates a cable system in which only one winding drum is provided, the other end being fixed as at 78. However, as previously mentioned, the latter end portion of the cable could be oppositely wound on a second drum also fixed to the drive shaft 33. The position of the magnetic transducer, represented by the resonator 34, is indicated midwaay of one section of the cable 32.

Figure 6:
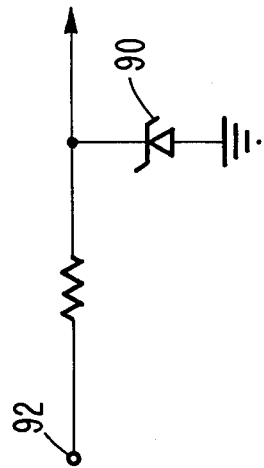
FIG. 6 is a detailed view of the circuit portion of the resonator oscillator employed in the circuit of FIG. 5.

FIG. 5 illustrates an oscillating circuit suitable for pulsating the magnetic field of the resonator 34. Included in the circuit is a unijunction transistor 80 which forms the basic oscillator whose frequency can be varied by use of an adjustable potentiometer represented at 82. For the purpose of measuring and setting the tension of stressed cables for the carriage 30 in the example illustrated in FIG. 1, the potentiometer may have a maximum resistance of 100 K which is capable in the illustrated circuit of adjusting the frequency of the oscillator from 300 to 600 Hz. A NAND gate 84 shapes the clock pulses to toggle the clock input flip flop 86. The flip flop emits square wave pulses of 0 to 5 volts and at half the frequency of the unijunction transistor 80 and all of one polarity. A NAND gate 88 forms the driver for the transducer coil 48 previously described and forming part of the resonator unit 34. This coil may have an ohmic resistance of 200 ohms. Included in the circuit of the resonator 34, as illustrated in FIG. 6, is a zener diode 90 which produces +5V for the IC logic from a voltage source 92 of 12 volts. A frequency monitor connector indicated at 94 may be employed to display the pulsed output of the oscillator on a frequency counter.

When using the apparatus hereinabove described for measuring the tension of a stressed element, an intermediate portion of the element is enclosed by the air gap 42 of the resonator 34. A desirable location for the application of the resonator for the looped cable 32 of the example illustrated in FIG. 1 is midway of one of the half sections of the cable. The oscillator 40 is operated to provide a pulsating magnetic flux field in the air gap which will oscillate the element. The potentiometer 82 is varied to vary the frequency of the oscillator and the magnetic field produced thereby until a condition of resonance exists in the stressed element which is clearly evidenced by the wide vibration thereof in the air gap such as represented by the dotted position of the cable 32 in FIG. 2. When this condition of resonance is reached for the cable of FIG. 1, a resonant vibrating displacement of approximately 0.050 to 0.060 inch. will occur which will be clearly visible to the operator. The vibrating string formula, frequency = $(2 \times \text{length})^{-1} (\text{tension/mass})^+$ is used to establish the above condition. For a particular cable, the curve of tension and resonant frequency can be calibrated and found to be linear within a range of forces applied to stress the cable, such as from 3.0 to 8.0 lbs. in the case of a Bergen cable. The tension vs. resonant frequency relationship can be plotted and a table prepared for various types of cables and other elements subject to axial stress. The following formula may be used for determining factors in this relationship: Tension (lb.) = $0.04426 \times$ Frequency (Hz)$-4.780$ or Frequency (Hz) = $22.5948 \times$ Tension (lb.) + $108.0779$.

When using the apparatus described hereinabove for setting a stressed element at a desired tension, an intermediary portion of the element is enclosed within the air gap 42 of the resonator 34. The coil 48 of the resonator is driven from the square wave oscillator 40 causing the magnetic field to intermittently attract the cable at the driving frequency of the oscillator. From the previously mentioned table calibrated for the particular stressed element or cable, the tension of the element or cable at its condition of resonance can be ascertained. Setting the oscillator at the frequency for this resonant condition, the operator can then vary the tension of the stressed element until a condition of resonance is exhibited in the air gap. When such occurs, the element has been tensioned to the desired amount and thereafter may be fixed or set at such stressed condition represented by its resonant frequency. In the example illustrated herein, such setting may take place by tightening the nuts 70—70 on their respective studs 64—64 to rigidly clamp the pulley carrying plate 62 in the desired adjusted position on the track member 28. It is apparent from the arrangement illustrated in FIG. 1 for mounting the stressed element that the operations of measuring or setting the stressed element may be performed in the absence of current flow through the element. There is no need to apply a potential drop across that portion of the stressed element extending through the gap for producing a current flow therethrough In lieu of a force gage 14 and its screw 16 for varying the tension of a stressed element or cable 32, other means may be provided for shifting the plate 62 relative to the track member 28 to vary the tension on the cable. One such means may be a wedge element capable of being interposed between the end of the plate 62 opposite to the pulley 50 and a stationary abutment formed on the track member. When the nuts 70—70 are loosened the wedge can be slowly advanced by a screw between the plate and the abutment in the direction to gradually increase the tension on the cable until the condition of resonance is observed in the air gap 42. When such occurs, the plate 62 may then be rigidly secured to the track member thus setting the stressed cable at the desired tensioned condition. A wedging tool of this character provides a simple expedient for production line usage. All like cables can have their tension similarly adjusted with the result that all usch cables act the same in either the same or similar equipment.

Although the invention is intended primarily for acting upon wire-like elements composed of material which is magnetically permeable, it is possible to adapt the invention for vibrating non-magnetic elements of this wire-like character by wrapping a part of the element with a shim of magnetic permeable material and disposing such part of the element in the air gap of the magnetic transducer.

While a paricular embodiment of the invention has been shown and described, it will be understood, of course, that it is not desired that the invention be limited thereto since modifications may be made and it is therefore contemplated by the appended claims to cover any such modifications as fall within the true spirit and scope of the invention

What is claimed is:

1. The method of setting a stressed element at a desired tension which includes the steps of subjecting an intermediate portion of the stressed element to a magnetic flux field pulsating in one polarity at a given frequency and in the absence of electrical current flow through the element thereby to cause the element to oscillate at the given frequency of the magnetic field, and varying the tension of the stressed element while subject to such pulsating magnetic field until a condition of resonance is exhibited by the element.

2. The method as set forth in claim 1 including the subsequent step of setting the stressed element in the tensioned condition represented by its resonant frequency.

3. The method as set forth in claim 1 wherein said given frequency is the natural resonant frequency of the element.

4. Apparatus for setting a wire-like element which is responsive to magnetic fields at a desired tensioned condition which includes, in combination:

a magnetic transducer having an air gap for receiving such an element and being of a size to permit the element to vibrate freely therein at its resonant frequency, means for mounting a wire-like element so as to extend through the air gap of the magnetic transducer and without a potential drop across that portion of the element extending through the gap, means for producing a pulsating magnetic flux field in said air gap operating at the frequency coinciding with the resonant frequency of the element received therein, and means for varying the tension of the element while subjected to the pulsating magnetic field until the condition of resonance is exhibited by the element.

5. The apparatus as set forth in claim 4 characterized in that means is provided for rigidly mounting the wire-like element in the tensioned condition represented by its exhibited resonant frequency.

6. The apparatus as set forth in claim 4 characterized in that the magnetic transducer includes an energizing coil and in that said pulsating magnetic field producing means is an oscillator circuit electrically connected to the coil of the transducer.

7. The apparatus as set forth in claim 6 characterized in that the oscillator circuit includes means for delivering square wave pulses of one polarity to the coil of the magnetic transducer.

8. In apparatus for affecting the tensioning of a magnetically responsive wire-like element wherein means is provided for mounting such element in tensioned condition, the combination including:

a magnetic resonator including an energizing coil enclosing a portion of a body of magnetic material having an air gap for receiving such a tensioned element, the air gap being of a size to permit the portion of the element received therein to accommodate the displacements of the element at its natural frequency, and an oscillator circuit connected to the coil and operable to produce uniformly spaced apart current pulses of one polarity in the coil for generating a pulsating magnetic field of the same frequency in the air gap.

9. The apparatus as set forth in claim 8 characterized in that means is provided for rigidly mounting such element in the tensioned condition represented by its natural frequency.

10. Apparatus for affecting the tension of a magnetically responsive wire-like element comprising, in combination:

a magnetic resonator including an energizing coil enclosing a portion of a body of magnetic material having an air gap for receiving such an element, the air gap being of a size to permit the portion of the element received therein to accommodate the displacements of the element at its natural frequency, means for mounting a wire-like element so as to extend through the air gap of the magnetic resonator and without the application of a potential drop over that portion of the element extending through the gap, an oscillator circuit connected to the coil and operable to produce current pulses in the coil of substantially square shape and all of one polarity for generating a pulsating magnetic field of the same frequency in the air gap, means in the oscillator circuit for varying the frequency of the current pulses delivered to the coil for similarly varying the frequency of the magnetic field generated in the air gap, and means for varying the tension of the wire-like element received in the air gap of the magnetic resonator while subjected to the pulsating magnetic field generated in the air gap.

* * * * *

UNITED STATES PATENT OFFICE
CERTIFICATE OF CORRECTION

PATENT NO. : 3,942,369

DATED : March 9, 1976

INVENTOR(S) : Edwin O. Roggenstein, Donald A. Andrews, and Chockalingam Manthiram It is certified that error appears in the above-identified patent and that said Letters Patent are hereby corrected as shown below:

Col. 4, lines 3 and 4, delete "forward are mounted on the fixture illustrated in Fig. 1, the" (second occurrence).

Col. 5, line 30, should read --$(tension/mass)^{+\frac{1}{2}}$--.
Col. 6, line 20, should read --such cables--.
Col. 6, line 31, should read --a particular embodiment--.

Signed and Sealed this eleventh Day of May 1976

[SEAL]

Attest:

RUTH C. MASON
Attesting Officer

C. MARSHALL DANN
Commissioner of Patents and Trademarks